(12) United States Patent
Dowd et al.

(10) Patent No.: US 10,551,288 B2
(45) Date of Patent: Feb. 4, 2020

(54) ROTARY BLADE SHARPNESS TESTING DEVICE

(71) Applicant: Anago Limited, Hamilton (NZ)

(72) Inventors: Peter Dowd, Hamilton (NZ); Stefan Van Woerden, Hamilton (NZ)

(73) Assignee: Anago Limited (NZ)

(*) Notice: Subject to any disclaimer, the term of this patent is extended or adjusted under 35 U.S.C. 154(b) by 216 days.

(21) Appl. No.: 15/527,791

(22) PCT Filed: Nov. 18, 2015

(86) PCT No.: PCT/NZ2015/050194
§ 371 (c)(1),
(2) Date: May 18, 2017

(87) PCT Pub. No.: WO2016/080848
PCT Pub. Date: May 26, 2016

(65) Prior Publication Data
US 2018/0313731 A1    Nov. 1, 2018

(30) Foreign Application Priority Data

Nov. 18, 2014    (NZ) .......................... 702079

(51) Int. Cl.
*G01N 3/58*    (2006.01)
*G01L 5/00*    (2006.01)

(52) U.S. Cl.
CPC .............. *G01N 3/58* (2013.01); *G01L 5/0061* (2013.01); *G01N 2203/0617* (2013.01)

(58) Field of Classification Search
CPC .......... G01L 5/0061; G01N 2203/0617; G01N 2203/0623; G01N 3/58
See application file for complete search history.

(56) References Cited

U.S. PATENT DOCUMENTS

| | | | | |
|---|---|---|---|---|
| 4,178,797 A | * | 12/1979 | Kozlowski, Jr. ......... | G01N 3/58 73/104 |
| 5,181,416 A | * | 1/1993 | Evans ..................... | G01N 3/58 73/104 |
| 5,379,633 A | * | 1/1995 | Flisram ................. | G01L 5/0028 73/104 |
| 5,571,040 A | * | 11/1996 | Kawaguchi .......... | B23D 59/002 451/11 |
| 5,571,956 A | * | 11/1996 | Sargent ................... | G01N 3/58 73/104 |

(Continued)

*Primary Examiner* — Francis C Gray
(74) *Attorney, Agent, or Firm* — Gloria Tsui-Yip; Gottlieb, Rackman & Reisman, P.C.

(57) ABSTRACT

A rotary blade sharpness tester is provided. The rotary blade sharpness tester comprises a rotary blade holder, supporting means for supporting a cuttable material, a moving mechanism to cause relative movement between the blade holder and the supporting means, and hence the cuttable material when supported on the supporting means, an activation means to activate a rotary blade held in the rotary blade holder and cause rotation of the blade before the blade comes into contact with the cuttable material. During the relative movement between the blade holder and supporting means the rotary blade movably contacts the material. The sharpness tester further comprises force measuring means operable in use to measure the force of the rotary blade on the cuttable material.

12 Claims, 8 Drawing Sheets

(56) References Cited

U.S. PATENT DOCUMENTS

| | | | |
|---|---|---|---|
| 2006/0201237 A1* | 9/2006 | Dowd | G01N 3/58 73/104 |
| 2007/0142959 A1* | 6/2007 | Rummel | B26D 7/12 700/160 |
| 2013/0186190 A1* | 7/2013 | Newell | G01N 19/08 73/104 |
| 2016/0069785 A1* | 3/2016 | Brubacher | G01N 3/58 73/104 |
| 2018/0321119 A1* | 11/2018 | Yin | G01N 3/56 |
| 2018/0333878 A1* | 11/2018 | Sonnenberg | B26B 21/4081 |

* cited by examiner

ROTARY BLADE SHARPNESS TESTING DEVICE

FIELD OF INVENTION

The invention relates to the field of blade sharpness testing devices and in particular to a device for testing the sharpness of a rotary blade.

BACKGROUND

Rotary knives such as the Whizard blades produced by Bettcher Industries Inc. are used primarily in the meat processing industry.

The rotary knives have a circular housing with an annular blade located within the housing. The rotary knife has cover plate located within the housing and next to a handle. The rotary knife is powered to cause the annular blade to rotate. Power is provided electrically or pneumatically or by some other method through the handle of the knife.

When knives are used the blade sharpness decreases over time. While blades can be sharpened periodically, it is more efficient to test whether a blade needs to be sharpened before sharpening the blade. Additionally it would be useful to be able to test whether the blade sharpening process is efficient.

It is the object of a preferred embodiment of the present invention to provide a rotary blade sharpness testing device or to at least provide a useful choice.

The term "comprising", if and when used in this document, should be interpreted non-exclusively. For example if used in relation to a combination of features it should not be taken as precluding the option of there being further unnamed features.

SUMMARY OF THE INVENTION

In broad terms in one aspect the invention comprises an annular blade sharpness tester comprising: an annular blade holder, supporting means for supporting a cuttable material, a moving mechanism to cause relative movement between the blade holder and the supporting means, and hence the cuttable material when supported on the supporting means, an activation means to activate an annular blade held in the annular blade holder and cause rotation of the blade before the blade comes into contact with the cuttable material, whereby during the relative movement between the blade holder and supporting means the rotary blade movably contacts the cuttable material, and force measuring means operable in use to measure the force of the annular blade on the cuttable material.

Preferably the moving mechanism moves both substantially horizontally and substantially vertically.

Preferably the force measuring means are one or more load cells.

Preferably the moving mechanism moves the blade downwards onto the cuttable material.

Preferably the supporting means is a mounting arrangement for mounting the cuttable material.

Preferably the cuttable material is held lightly over one or more load cells.

Preferably the cuttable material is tensioned using a motor of the mounting arrangement and clamps.

In one embodiment the load cell(s) is/are positioned on top of upright rods. In another embodiment the load cell(s) is/are positioned on a clamp.

In one embodiment one load cell is provided on top of the upright rods and on each side of the cuttable material. In another embodiment a load cell is provided on top of one side of a clamp and cuttable material.

Preferably the upright rods are positioned with a central gap so the rotary blade can fit around at least one rod.

Preferably the cuttable material is positioned over the gap between the upright rods.

Alternatively the cuttable material is positioned on sprockets including over a gap between the sprockets.

Preferably force measurements are sent to a computer or processed in the machine.

In broad terms in another aspect the invention comprises a method of testing the sharpness of an annular blade comprising the steps of: a) positioning the annular blade in a blade housing, b) placing the blade housing in a blade holder, c) powering the blade so that it rotates, d) causing relative movement between the blade holder and a cuttable material supported on a supporting means, e) measuring the force on the cuttable material when the rotating blade comes into contact with the cuttable material, and f) estimating the blade sharpness from the measured force.

DRAWINGS

The invention will be further described with reference to the accompanying drawings in which.

DETAILED DESCRIPTION

Some preferred forms of the invention will now be described by way of example. It should be understood that these are not intended to limit the scope of the invention but rather to illustrate optional embodiments.

Figure 1:
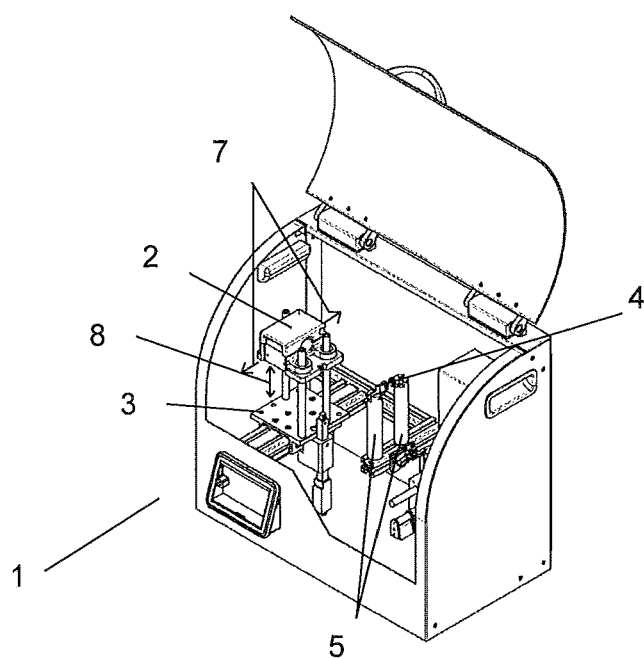
FIG. 1 shows the top right view of a rotary blade sharpness testing machine.

FIG. 1 shows a rotary blade sharpness testing machine 1. The blade sharpness testing machine includes a rotary blade holder 2, mounting arrangement for a cuttable strip (shown in FIG. 2), moving mechanism 3, load cells 4 mounted on rods 5.

The machine may be contained within a housing. In FIG. 1 the housing is shown with a see-through lid that allows observation of the testing. The lid is hinged with hinges 6 to allow access into the machine to place rotary blades in the machine and remove rotary blades from the machine.

Rotary blade holder 2 holds a rotary blade housing by the handle so that the blade extends towards rods 5. The blade holder 2 is adapted to hold the handle of a rotary blade housing such that in use the blade can be moved over one of the rods.

Figure 2:
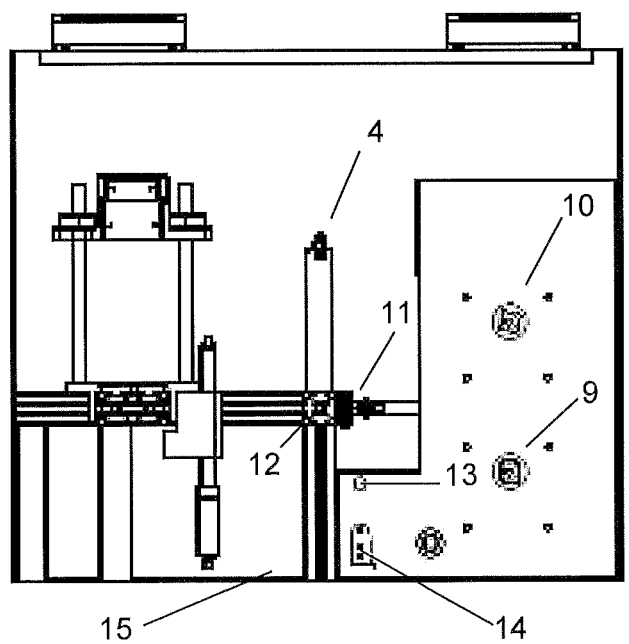
FIG. 2 shows a front view of a rotary blade sharpness testing machine.
Figure 3:
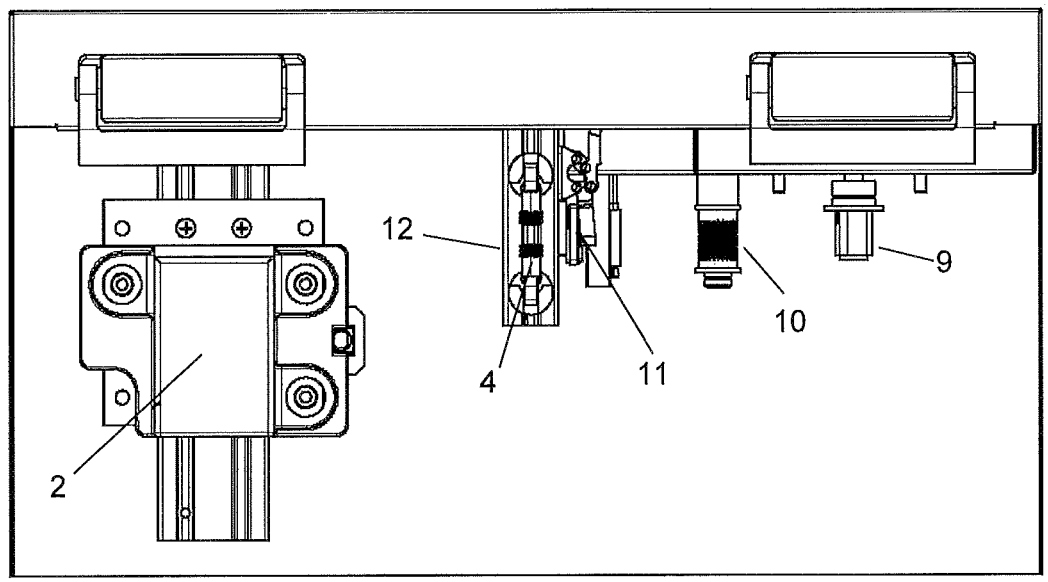
FIG. 3 shows a top view of a rotary blade sharpness testing machine.

The moving mechanism 3 is able to move the rotary blade and blade holder in both the substantially vertical and substantially horizontal directions as shown by arrows 8 and 7 respectively. This allows the rotary blade to be positioned for the sharpness test and to be moved away from the test area for ease of removal from the testing machine. FIG. 2 shows the blade holder 2 away from rods 5.

Rods 5 extend substantially vertically within the machine. Rods 5 are dimensioned to be able to extend through the circular opening in a rotary blade housing. The circular opening of the rotary blade housing of the rotary knife may have diameter between 30 and 120 mm.

Load cells 4 are positioned on top of rods 5. The load cells are arranged to measure the force on top of the load cell. Data from the load cell is sent to a computer by any suitable means. For example, the data may be sent to a computer via a serial cable or processed in the machine using an on-board processing chip.

In this embodiment two load cells are provided. The cuttable strip rests lightly on the load cells. FIG. 2 shows a side view of the blade sharpness testing machine of the invention. The cuttable material extends from a spool on connector 10, around roller 13, through clamp 11, lightly resting on load cells 4, past rod base 12, through upside down u section 15, through roller 14 to a spool on connector 9. Connectors 9 and 10 may be able to be independently driven by a motor in the machine. Clamp 11 is used to tension the cuttable material along with the motor adapted to drive connector 9.

The machine also includes a means to activate the rotary blade. This means may be any suitable power means for the blade and an operator controlled switch so that the blade is only rotating during the test.

Figure 4:
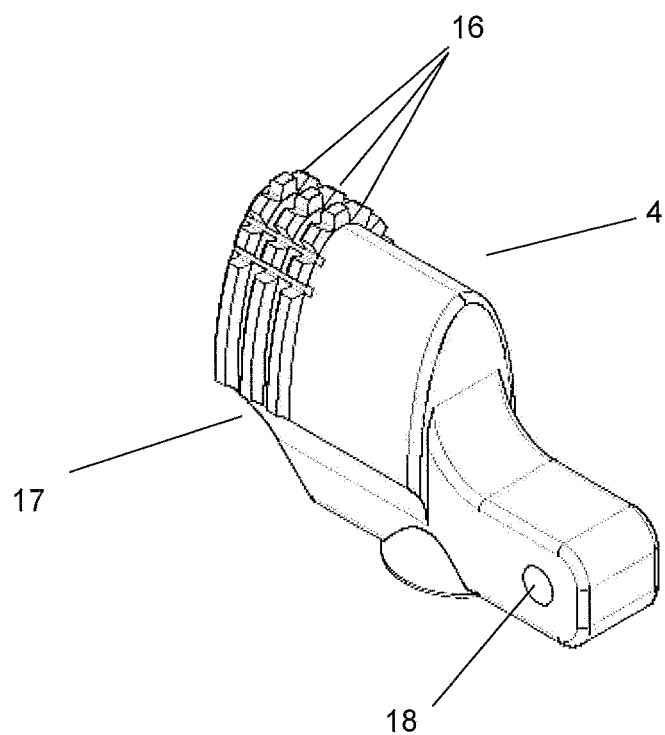
FIG. 4 is a perspective view of a load cell used in the rotary blade sharpness testing machine.

FIG. 4 is a perspective view of an embodiment of load cell 4 that forms part of the rotary blade sharpness testing machine. The load cell includes a plurality shaped blocks 16 adapted to interlock with the cuttable material to hold the cutting strip in place and enable a strong and consistent grip on the cuttable material during testing of a rotary blade. Ideally the shaped blocks 16 are shaped to match the curvature of the cuttable material so that maximum contact between the load cells and cuttable material is maintained during testing of a rotary blade.

In preferred embodiments the load cell 4 is able to pivot about pivot point 18. Once a blade has finished its test cut the blade may be located below the load cell in the sharpness testing machine. The blade is then raised. If the blade contacts the load cell 4 as the blade is being raised the load cell may pivot to avoid damage to the load cell and allow the blade to be raised. Angled surface 17 on load cell 4 provides a surface against which the blade may contact as it is being raised.

Ideally the cuttable material is a strip of mesh with a plurality of independent lines of material spanning with width of the strip. This means that during testing when the rotary blade cuts through one independent line it must begin again on the next independent line. If the lines were not independent then once cutting began the force required to cut the cuttable material would decrease from the initial force required. With independent lines the force required to cut each line is the same.

In one embodiment the mesh is formed from fabric and plastic. However, any suitable construction of mesh may be used. Ideally the mesh and shaped blocks on the load cells 4 correspond to allow maximum contact between the mesh and the load cells during testing of a rotary blade.

Figure 5:
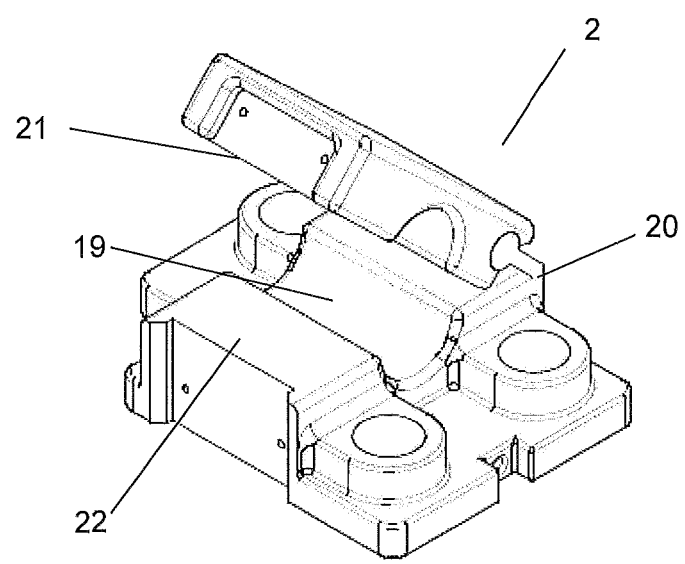
FIG. 5 is a perspective view of a rotary blade holder used in the rotary blade sharpness testing machine.

FIG. 5 shows a rotary blade holder 2 adapted to hold a rotary blade housing (not shown) during testing. The rotary blade holder 2 includes aperture 19 shaped to enclose the shaft of the rotary blade and hinge means 20. Hinge means 20 may be any suitable means that allows the rotary blade holder to open and close around the shaft of the rotary blade housing. In FIG. 5 hinge means 20 is in the open position. In the closed position surfaces 21 and 22 contact each other and a suitable means (not shown) is provided to hold the blade holder closed. The rotary blade housing extends from the blade holder so that it will contact the cuttable material when the machine is activated.

An on-board processor may be provided in the machine. If a processor is provided the processor may process data from the load cells during or after cutting of the cuttable material by a rotary blade under test. The processor may also be used to control the raising and lowering of the holder to determine how far the rotary blade will travel during contact with the cuttable material. If the diameter of the rotary blade is provided to the on-board processor then the circumference of the blade can be readily determined. Given the speed at which the blade is lowered when in contact with the cutting surface the processor can determine how far to lower the blade so that all parts of the rotary blade will come into contact with the cuttable material. In this way the entire length of the blade will be used to cut the cuttable material and differences in sharpness along the blade will be shown by a change in force on the load cells as the blade cuts the cuttable material. Changes in the force on the load cells during cutting may indicate that a portion of the blade is not as sharp as other portions of the blade. This may in turn indicate that the blade sharpening process needs adjustment. Alternatively control of the distance that the blade will travel can be via a connected processor or made manually.

Figure 6:
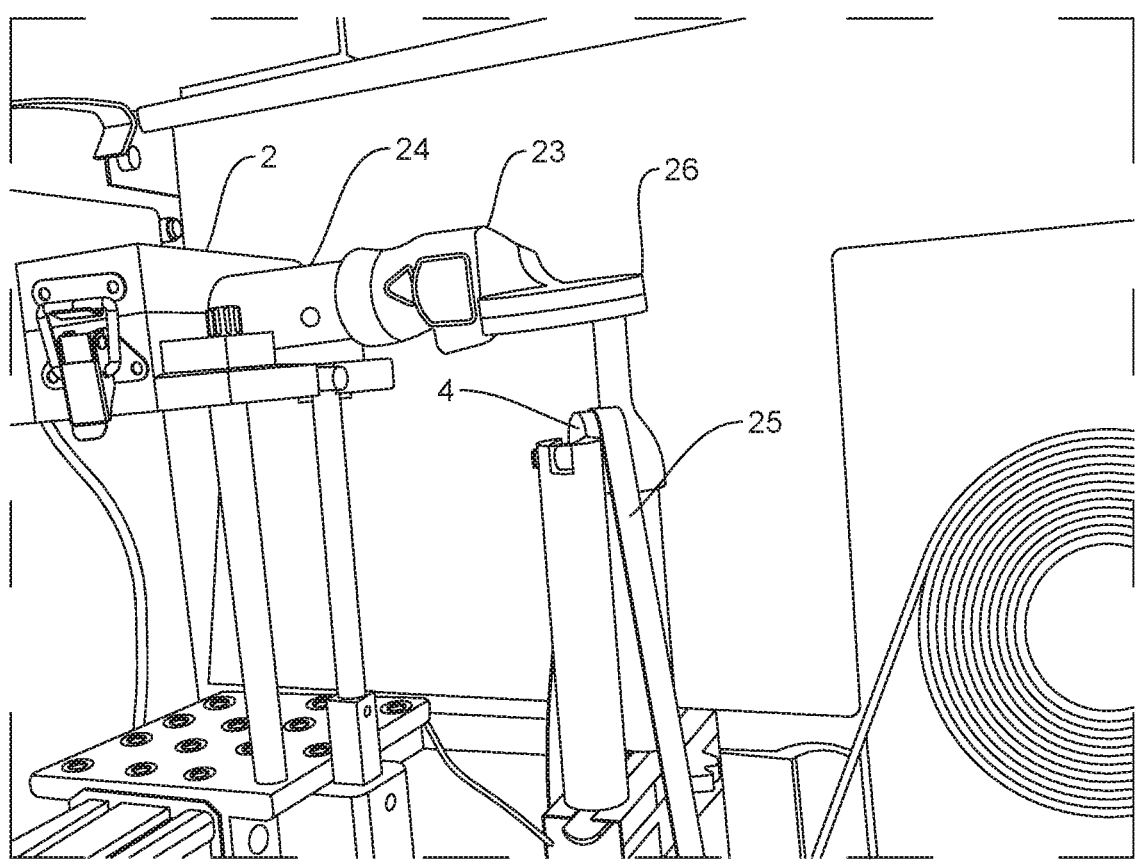
FIG. 6 is a close up view showing part of the rotary blade sharpness testing machine.
Figure 7:
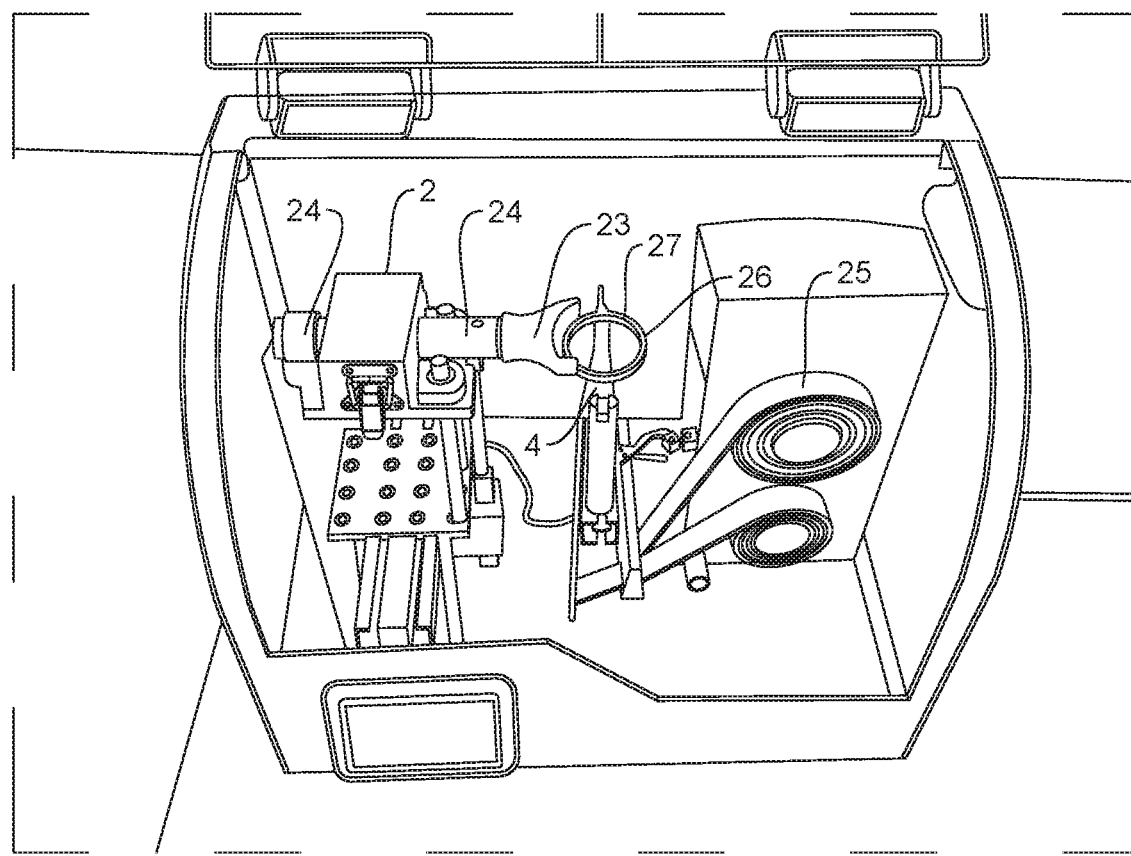
FIG. 7 is a top view of the rotary blade sharpness testing machine with a rotary blade.

FIGS. 6 and 7 show a rotary blade sharpness testing machine with a rotary blade 23. The rotary blade 23 comprises a shaft 24, a blade housing 26 and blade 27 (best seen in FIG. 7). Blade 27 is housed within blade housing 26. Power is provided to blade 27 through shaft 24. When the rotary blade is activated, blade 27 rotates within housing 26. In FIGS. 6 and 7 the shaft 24 is housed in housing 2 and blade housing 26 (and therefore blade 27) is located above cuttable material 25.

In use a rotary blade housing including a rotary blade is loaded into the rotary blade holder so that it extends towards the rods. The blade holder is raised (if necessary) moved towards the rods so that when lowered the rotary blade will come into contact with the cuttable material and one rod will pass through the circular housing of the rotary blade. The blade is activated and the housing lowered so that the blade comes into contact with the cuttable material. Load cells 4 measure the force of the blade on the cuttable material. Eventually the blade will begin to cut the cuttable material. The blade is lowered onto the cuttable material so that all of the blade surface cuts the cuttable material. During this time the force on the load cells is measured. The force on the load cells may be processed in the machine, stored in the machine or sent to a processor for processing. After the test the blade is raised and deactivated. The blade can be moved away from the rods and the load cells. Data from the load cells is sent to a computer or other suitable data processing device. The motors are activated to spool the cuttable material from spool 10 to spool 9 so that an uncut section of cuttable material is positioned over the load cells. Once the data is processed an indication of sharpness of the blade may be given.

Figure 8:
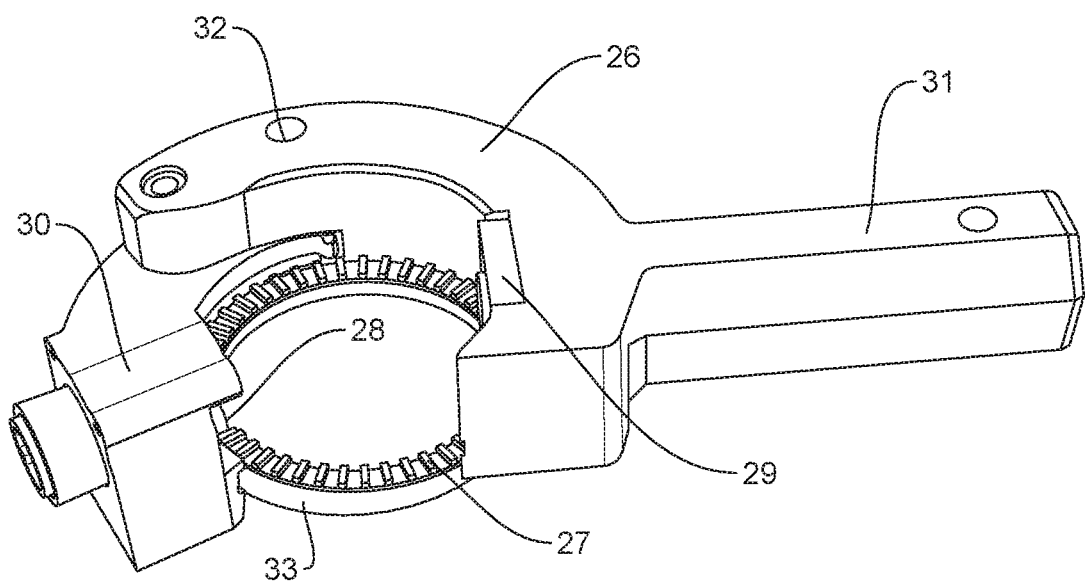
FIG. 8 shows a blade housing.

FIG. 8 shows an embodiment of blade housing 26. The blade housing houses blade 27, sprockets 28 and 29 as well as side 30, a pivot point 32 and a handle 31.

In the embodiment of blade housing shown in FIG. 8 the handle 31 has a hexagonal cross section. The blade holder can then have a complementary hexagonal opening into which the handle slides or sits. The advantage of this design is that the handle can be positioned in the holder and is held in place by the handle sides siting against the holder sides. The handle can also be removed from the holder and rotated before replacement in the holder to allow different surfaces of the cutting blade to be tested. Although in this embodiment the handle 31 has a hexagonal cross section, in other embodiments the handle could have a different cross section—for example octagonal.

The blade 27 in the blade housing 26 may be supported by a circular or semi-circular support 33. The blade 27 includes ridges on its upper surfaces. These ridges engage with sprockets 28 and 29. Sprocket 29 is powered and rotates to drive the blade 27. Power is provided to sprocket 29 by any suitable means. Sprocket 28 provides support to the blade 27 to keep the blade in place. This sprocket may be freewheeling and not powered. The support ring 33 may be circular or semi-circular.

The blade housing may include a side 30 that can pivot about pivot point 32 to allow easy access to the blade 27 inside the housing 26. When a blade has been placed in the blade holder the side 30 can be rotated into the position shown in FIG. 8 and locked into place. When the blade is to be changed the side 30 can be unlocked and rotated about pivot point 32 to allow access to the blade 27 for removal.

Figure 9:
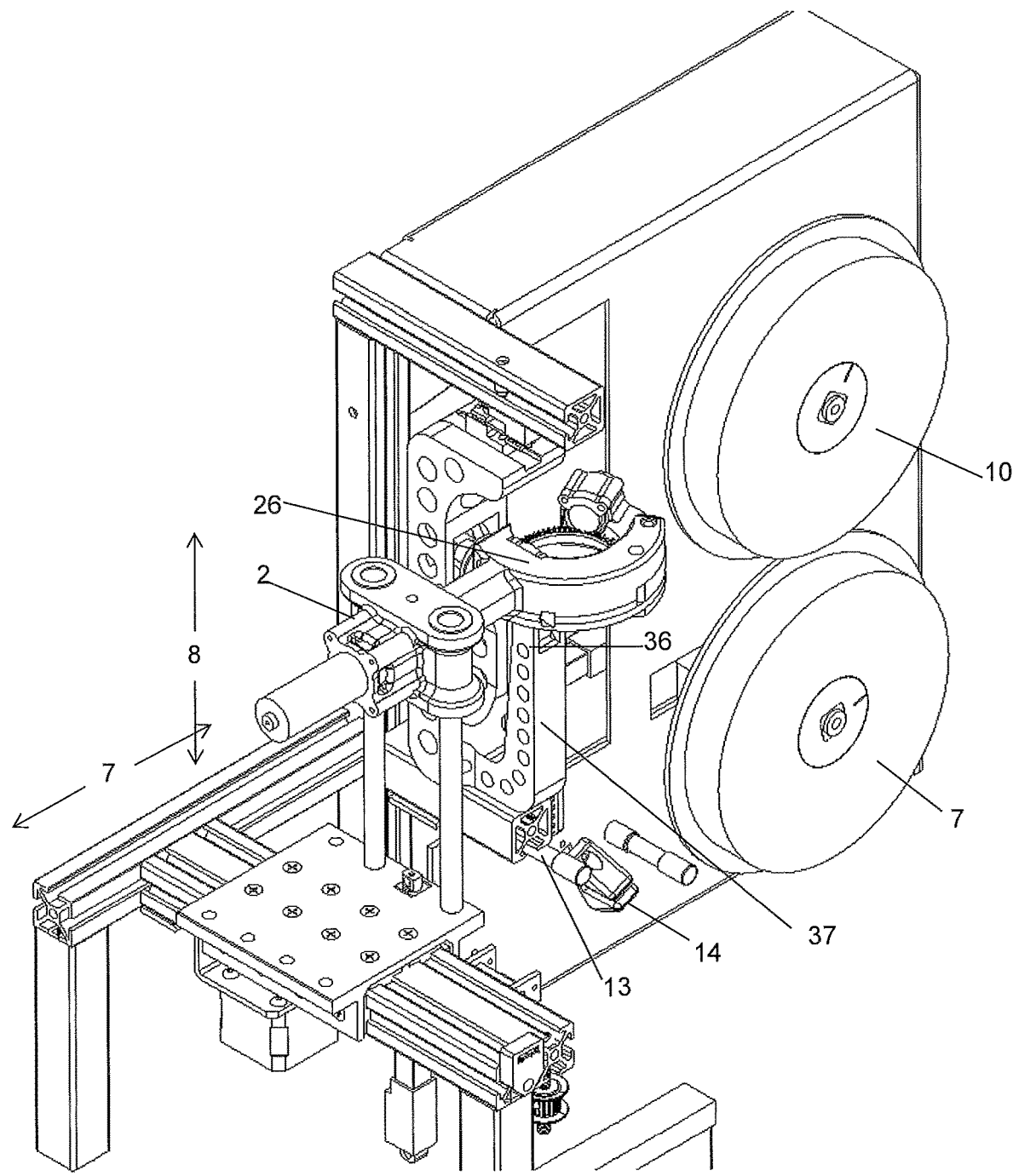
FIG. 9 is a perspective view of a second embodiment of rotary blade sharpness testing machine.
Figure 10:
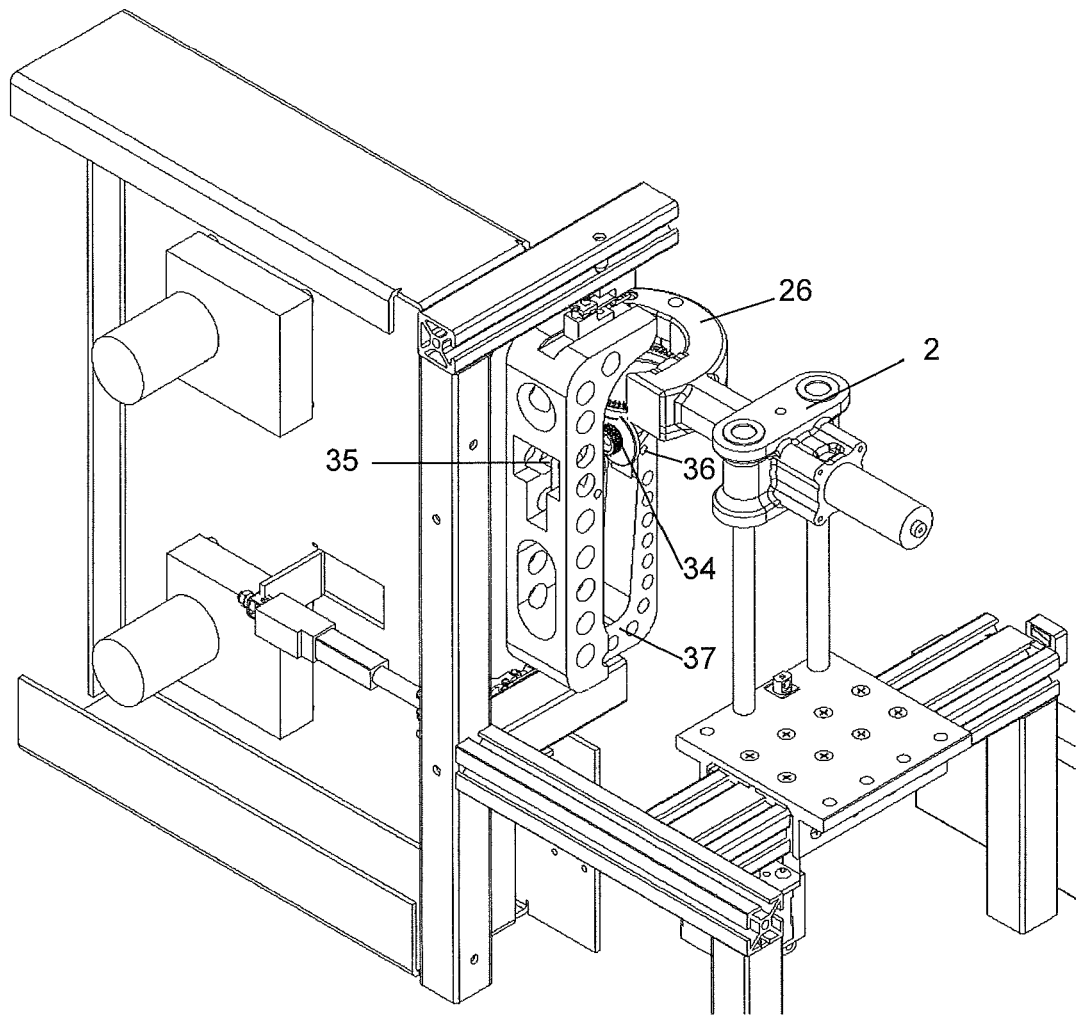
FIG. 10 is a second perspective view of the second embodiment of rotary blade sharpness testing machine.
Figure 11:
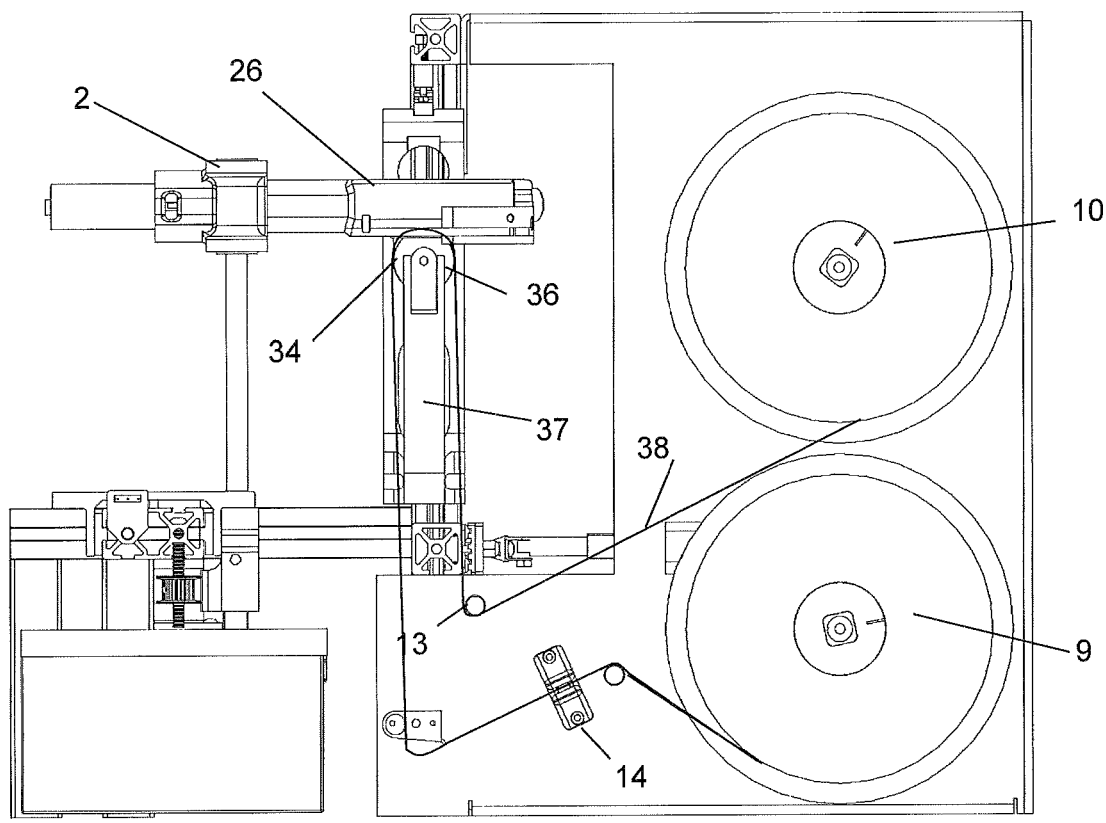
FIG. 11 is a side view of the second embodiment of rotary blade sharpness testing machine.

FIGS. 9, 10 and 11 show a second embodiment of rotary blade sharpness testing machine. The testing machine includes a rotary blade holder 2, mounting arrangement for a cuttable strip, load cell (not shown) mounted on a G clamp 37. Like the first embodiment, the machine may be contained within a housing (not shown).

Rotary blade holder holds a rotary blade housing of the type described with reference to FIG. 8 or may hold a rotary blade housing with a substantially cylindrical handle. The blade holder holds the rotary blade by the handle so that the blade extends towards the toothed sprockets 34, 35 (shown in FIG. 10) held by the G clamp 37.

The moving mechanism is able to move the rotary blade and blade holder in both the substantially vertical and substantially horizontal directions as shown by arrows 8 and 7 (see FIG. 9) respectively. This allows the rotary blade to be positioned for the sharpness test and to be moved away from the test area for ease of removal from the testing machine.

The blade is tested by being moved into contact with a cuttable material. In this embodiment the cuttable material runs over the toothed sprockets 34 and 35 that are attached to the G clamp 37. The toothed sprockets are able to rotate freely about their axes.

G clamp 37 is attached to a frame of the blade sharpness testing machine. The G clamp 37 holds the toothed sprockets 34 and 35 substantially opposite each other. A cuttable material 38 (shown in FIG. 11) extends from connector 10, around guide 13 across the sprockets 34 and 35 coming into contact with a portion of the teeth of the sprockets before passing around various rollers and guides (including guide 14) to connector 7. The G clamp holds the sprockets in a spaced apart relationship to allow the cuttable material 38 to sit on the sprockets and extend between the sprockets so that is can be used in testing. It should be noted that while in this embodiment the clamp is G shaped any shape can be used that holds the sprockets apart so that the cuttable material sits on some teeth of each sprocket and extends between them and allows access to the rotary blade. The G clamp is dimensioned so that the free end is able to extend through the circular opening in the rotary blade housing.

In this embodiment a single load cell (not shown) is provided on the free end of the G clamp 37 with sprocket 34. The load cell measures the force applied to the cuttable material and provides the force data to a processing system.

In addition to being freewheeling, sprockets 34 and 35 are able to pivot about pivot points 36 in the G clamp 37 (see FIG. 10). The sprockets can pivot upwards from the position shown in FIG. 10. The pivots allow the sprockets to move out of the way if the rotary blade holder 26 comes into contact with either sprocket after moving to below the sprocket level. FIG. 10 shows a cut out portion of the G clamp 37 behind sprocket 35 to allow the sprocket space to pivot.

In use a rotary blade is loaded into the rotary blade housing and the housing is positioned in the holder so that the holder extends towards the clamp. The blade holder is raised (if necessary) moved towards the clamp so that when lowered the rotary blade will come into contact with the cuttable material and a free end of the clamp will pass through the circular housing of the rotary blade. The blade is activated by any suitable power means and the housing lowered so that the blade comes into contact with the cuttable material. The load cell measures the force of the blade on the cuttable material. Eventually the blade will begin to cut the cuttable material. The blade is lowered onto the cuttable material so that the entire blade surface cuts the cuttable material. During this time the force on the load cell is measured. The force on the load cell may be processed in the machine, stored in the machine or sent to a processor for processing. After the test the blade is raised and deactivated. The blade can be moved away from the clamp and the load cell. Force data from the load cell is sent to a computer or other suitable data processing device. Once the force data is processed an indication or estimation of sharpness of the blade may be given. After the blade has been tested the housing is moved up and away from the clamp so that the blade can be removed. The motors are activated to spool the cuttable material from spool 10 to spool 9 so that an uncut section of cuttable material is positioned over the load cell.

In the claims which follow and in the preceding description of the invention, except where the context requires otherwise due to express language or necessary implication, the word "comprise" or variation such as "comprises" or "comprising" is used in an inclusive sense, i.e. to specify the presence of the stated features but not to preclude the presence or addition of further features in various embodiments of the invention.

While some preferred aspects of the invention have been described by way of example it should be appreciated that modifications and improvements can occur without departing from the scope of the invention as defined by the accompanying claims.

The invention claimed is:

1. An annular blade sharpness tester comprising:
   an annular blade holder,
   supporting means supporting a cuttable strip material either side of a gap, a moving mechanism that causes relative movement between the blade holder and the supporting means, and hence the cuttable strip material supported by the supporting means, an activation means that activates an annular blade held in the annular blade holder and causes rotation of the blade before the blade comes into contact with the cuttable strip material, and also causes relative movement between the blade holder and supporting means such that the annular blade movably contacts the cuttable strip material and cuts it at the gap, and force measuring means that measures the force of the annular blade on the cuttable strip material.

2. An annular blade sharpness tester according to claim 1, wherein the cuttable strip material comprises mesh.

3. An annular blade sharpness tester according to claim 2, wherein the mesh extends between two spools and is wound from one to the other.

4. An annular blade sharpness tester according to claim 3, wherein the supporting means comprises toothed sprockets opposite to and spaced from one another and the mesh runs over and extends between the sprockets.

5. An annular blade sharpness tester according to claim 4, wherein the sprockets are free wheeling and are arranged to pivot if contacted by the blade holder.

6. An annular blade sharpness tester according to claim 5, wherein the force measuring means comprises a load cell.

7. An annular blade sharpness tester according to claim 6, wherein the blade holder holds the blade such that the blade arcs across an opening of the blade holder.

8. An annular blade sharpness tester according to claim 7, comprising a clamp that tensions the mesh.

9. An annular blade sharpness tester according to claim 8, wherein the supporting means is generally G shaped.

10. An annular blade sharpness tester according to claim 9, wherein the blade holder is adapted to move towards a free end of the supporting means so that the free end will pass through the blade holder.

11. An annular blade sharpness tester according to claim 10, comprising a controller that controls raising and lowering of the blade holder to cause substantially all parts of the blade come into contact with the mesh.

12. An annular blade sharpness tester according to claim 1, wherein the blade holder holds the blade such that the blade arcs across an opening of the blade holder.

* * * * *